United States Patent [19]

Enoch et al.

[11] Patent Number: 4,798,456
[45] Date of Patent: Jan. 17, 1989

[54] METHOD FOR EVALUATING METAMORPHOPSIA

[75] Inventors: Jay M. Enoch, Moraga; Richard A. Knowles, Berkeley, both of Calif.

[73] Assignee: The Regents of the University of California, Berkeley, Calif.

[21] Appl. No.: 29,313

[22] Filed: Mar. 23, 1987

[51] Int. Cl.⁴ .............................................. A61B 3/02
[52] U.S. Cl. ................................. 351/222; 351/246; 351/224
[58] Field of Search ............... 351/222, 224, 225, 226, 351/243, 246

[56] References Cited

U.S. PATENT DOCUMENTS 3,025,755  3/1962  Koetting ............................ 351/243
3,837,734  9/1974  Regan ................................ 351/222

Primary Examiner—Rodney B. Bovernick
Assistant Examiner—Jay Ryan
Attorney, Agent, or Firm—Phillips, Moore, Lempio & Finley

[57] ABSTRACT

A hyperacuity testing method is suitably programmed for quantitatively measuring metamorphopsia of a patient's visual system, detecting and measuring metamorphopsia behind a media opacity, such as cataract, and detecting and measuring smaller amounts of metamorphopsia and other visual distortions than previously possible. The method comprises displaying at least two spaced and fixed first spots on a screen, along with a movable second spot. A patient is instructed to selectively move the second spot relative to the fixed first spots whereby the clinician is enabled to comparatively record separation distances and displacement of the second spot relative to the first spots.

10 Claims, 3 Drawing Sheets

METHOD FOR EVALUATING METAMORPHOPSIA

ACKNOWLEDGEMENT

This invention was made with Government support under Grant Contract No. R01 EY-03674, awarded by the National Institute of Health. The Government has certain rights in this invention.

TECHNICAL FIELD

This invention relates generally to a method for evaluating metamorphopsia and more particularly to a method using an Amsler Grid type approach for such evaluation.

BACKGROUND ART

The pre-surgical assessment of visual potential in eyes with occluded optical media is a challenge which often confronts the ophthalmic surgeon. Patients with corneal opacification, dense cataracts, and vitreal bleeds of the eye may exhibit reduced vision whereby estimating retinal and visual potential is at best inaccurate.

Various devices and attendant methods, such as the laser interferometer, the Potential Acuity Meter (PAM), and electro-physiological instruments, have been developed in response to this need. The former two methods, while useful in many cases, are ineffective unless a clear "window" exists in a particular opacity. The latter method yields information that must be interpreted with considerable caution because of difficulties encountered in distinguishing between responses originating from the fovea, as opposed to the surrounding retina, the effects of optical degradation on patterned stimuli, etc..

The aforementioned disadvantages do not apply to the use of hyperacuity tests of the type discussed in co-pending U.S. Application Ser. No. 028,711, filed on Mar. 20, 1987 by Jay M. Enoch, a co-inventor for herein, "Hyperacuity Testing Instrument for Evaluating Visual Function". First, performance on hyperacuity tasks has been shown to be much less affected by optical degradation produced by both simulated and real ocular opacities than is performance of resolution tasks. Indeed, no clear "window" in a media opacity is required. Second, because hyperacuity performance falls off rapidly with increasing retinal eccentricity, foveally vs. extrafoveally-based responses are difficult to confuse when they are compared.

Metamorphopsia refers to several forms of image distortion that patients may experience who exhibit certain forms of central retinopathy or choroidopathy and/or a history of retinal detachment, sub-retinal tumor or tractional lesions. To help analyze these disturbances of visual function (as well as to delineate the bounds of central scotomas and areas of distortion), the well-known Amsler Grid test is often employed.

The Amsler Grid is a square grid, usually 10 cm × 10 cm in size, having 5 mm × 5 mm individual "checkerboard" squares. The grid is normally held approximately 28 to 30 cm away from a patient for testing purposes. The individual squares will then subtend a visual angle closely approximating 1° or less. The squares are normally formed by while lines imprinted on a black background.

In use, a patient is asked to fixate on a spot in the center of the grid and while fixating on the spot is then asked to describe how the remainder of the grid appears. The patient is asked a series of questions in order to determine if the patient perceives missing or dim areas, whether lines are straight or wavy or crooked, etc. Usually the patient is asked to point to the defective areas the patient perceives on the grid. He/she may be asked to draw any distortions seen or to outline the area of distortion on a pad.

The degree of actual distortion is difficult to evaluate from such a test and no quantification is possible. Thus, it is difficult to evaluate modest changes in such patterns. In addition, this test pattern is of little or no use in the presence of significant ocular opacities because the grid lines become difficult to resolve, visually.

A measurement of the mean value of subjective vernier or bisection alignment, called the directional bias (or constant error), can be a sensitive indicator of metamorphopsia in many cases. One so-called "two-dot vernier" psychophysical hyperacuity test has been proposed to detect and quantify retinal distortions even in the presence of ocular opacities. This test is largely based on previous hyperacuity paradigms (gap test and perimetry test) which have been successfully applied to the detection of retinal/neural disorders behind cataracts or other ocular media opacities (corneal leukomas, vitreal membranes, and bleeds) and the evaluation of central visual acuity potential in the presence of such opacities.

Quantification of changes in an Amsler grid-type pattern is a useful goal in and of itself and is valuable to measure fine changes occurring in the presence of retinal anomalies without the added complications of occluded media.

DISCLOSURE OF THE INVENTION

This invention provides an improved method for evaluating metamorphopsia and other distortions of central and paracentral vision.

The method comprises the steps of displaying at least two first spots in fixed and spaced relationship relative to each other on a display screen, displaying a second spot on the display screen between the first spots, selectively moving the second spot relative to the first spots for observation and comment by a patient, and measuring the relative separation distances between the second spot and the first spots and the displacement of the second spot relative to an imaginary line intersecting the first spots.

The method can be expanded to include additional fixed first spots. At each point measured, the constant error (bias) and variance (or estimate of same), the hyperacuity estimate, can be measured, recorded and/or displayed as desired.

BRIEF DESCRIPTION OF THE DRAWINGS

Other advantages and objects of this invention will become apparent from the following description and accompanying drawings wherein.

BEST MODE OF CARRYING OUT THE INVENTION

Figure 1:
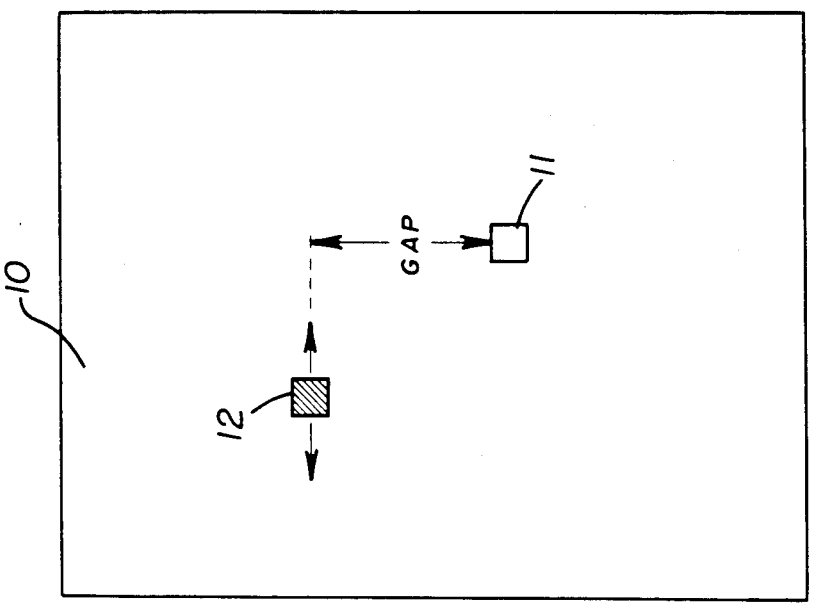
FIG. 1 illustrates a conventional two-dot vernier task display.

The conventional two-dot vernier task display shown in FIG. 1 constitutes a display screen 10 (e.g., TV screen or CRT), a fixed spot or dot 11 and a horizontally movable spot or dot 12. In this test, the patient is asked to vertically align movable spot 12 with fixed spot 11 by moving the movable spot horizontally. The spots are separated vertically by a variable distance ("gap"). When the patient perceives vertical alignment of the spots, the result is recorded to indicate error, if any. The terms "spot" and "dot" are used interchangeably herein and for purposes of this invention.

It is believed that individuals with retinal stretch or distortion, while having abnormally large directional biases, might exhibit either normal or abnormal vernier acuity, depending on the particular type of retinal involvement. In alignment-type tasks, such as the above two-dot vernier task, the variability the patient exhibits on repeated vernier trials (without feedback) is referred to as vernier acuity, one of the hyperacuities. The mean value of subjective alignment (constant error) is referred to as directional bias. These two quantities, vernier acuity and directional bias, are measured for various spot separations, thus generating a "map" of retinal spatial anomalies.

Figure 2:
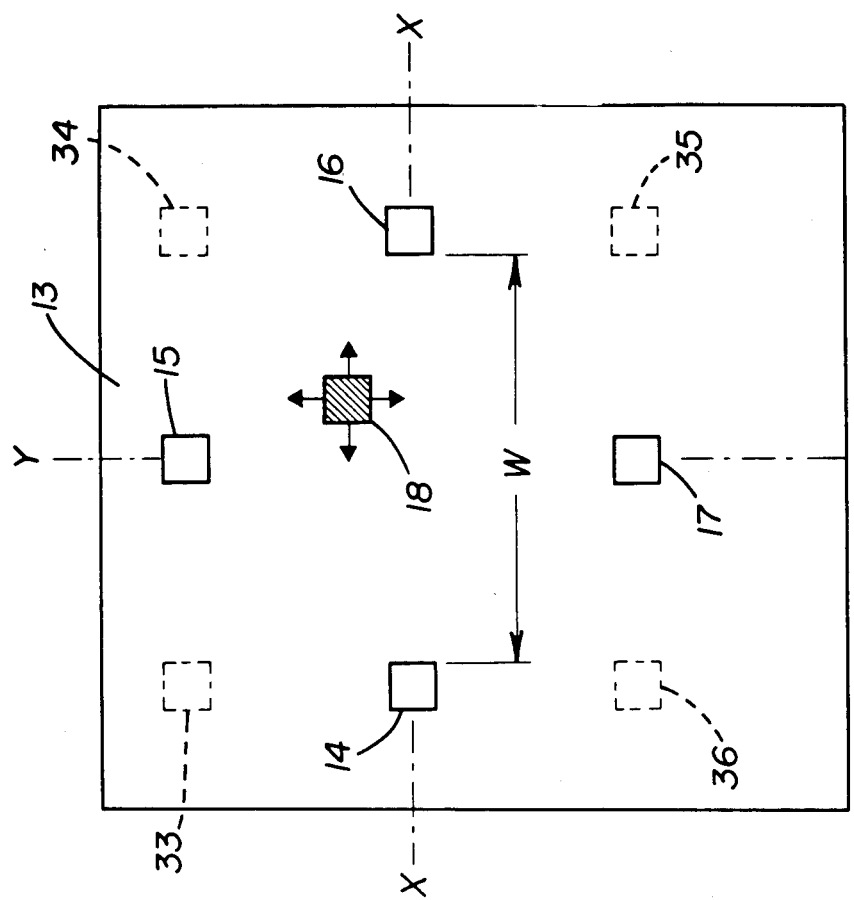
FIG. 2 illustrates a multi-dot hyperacuity bisection task display, used to carry forth a method of this invention.

The improved test or method of this invention can be best understood by reference to the multi-dot hyperacuity bisection display shown in FIG. 2. The display comprises a display screen 13 (e.g., a video monitor) displaying a pair of horizontally aligned fixed spots 14, 16, a pair of vertically aligned fixed spots 15, 17 and a movable spot 18 between the fixed spots. This stimulus configuration has been arranged to simultaneously provide quantitative information regarding distortion along both the imaginary perpendicular and intersecting vertical (Y) and the horizontal (X) axes of the screen. This test is similar in some respects to a simplified Amsler Grid test. However, one notable difference is that the central spot imprinted on an Amsler grid chart is fixed whereas spot 18 (FIG. 2) is adapted to be moved by the observer/patient. Further, on the Amsler Grid test, the points are usually connected by lines.

The patient may be, for example, requested to adjust the position of randomly decentered spot 18 to a position perceived as "true" vertical alignment (adjusting position in two dimensions) with spots 15 and 17 (Y axis), horizontal alignment with spots 14 and 16 (X axis) and/or disposition at the center of the cross-like pattern formed by four surrounding fixed spots 14-17 (intersection of axes X and Y). This paradigm represents a simultaneously-conducted dual bisection task. Spots 14-18, when computer induced, may constitute rectangular patches of light in the range of one to two arc min. on each side. The X and Y coordinates of the "subjective" relative location of spot 18 as perceived by the patient are averaged over several trials, i.e., the relative separation distances between the spots and the displacement of moveable spot relative to selected fixed spots is measured. The distance of the mean value of the subjective center (i.e., the two-dimensional directional bias) from the real center is a measurement of the metamorphopsia (or distortion) that may be present.

To determine the spatial element of an anomaly, the gaps between the spots are set at a discrete number of different values (separation distance W, between fixed spots 14, 16 and/or fixed spots 15, 17, may be varied from 1 to 9 degrees in 1 degree steps). If the patient is incapable of defining a unique center, the test may be divided into two separate bisection tests, (measured in two dimensions), namely, a horizontal task and a vertical task.

Figure 3:
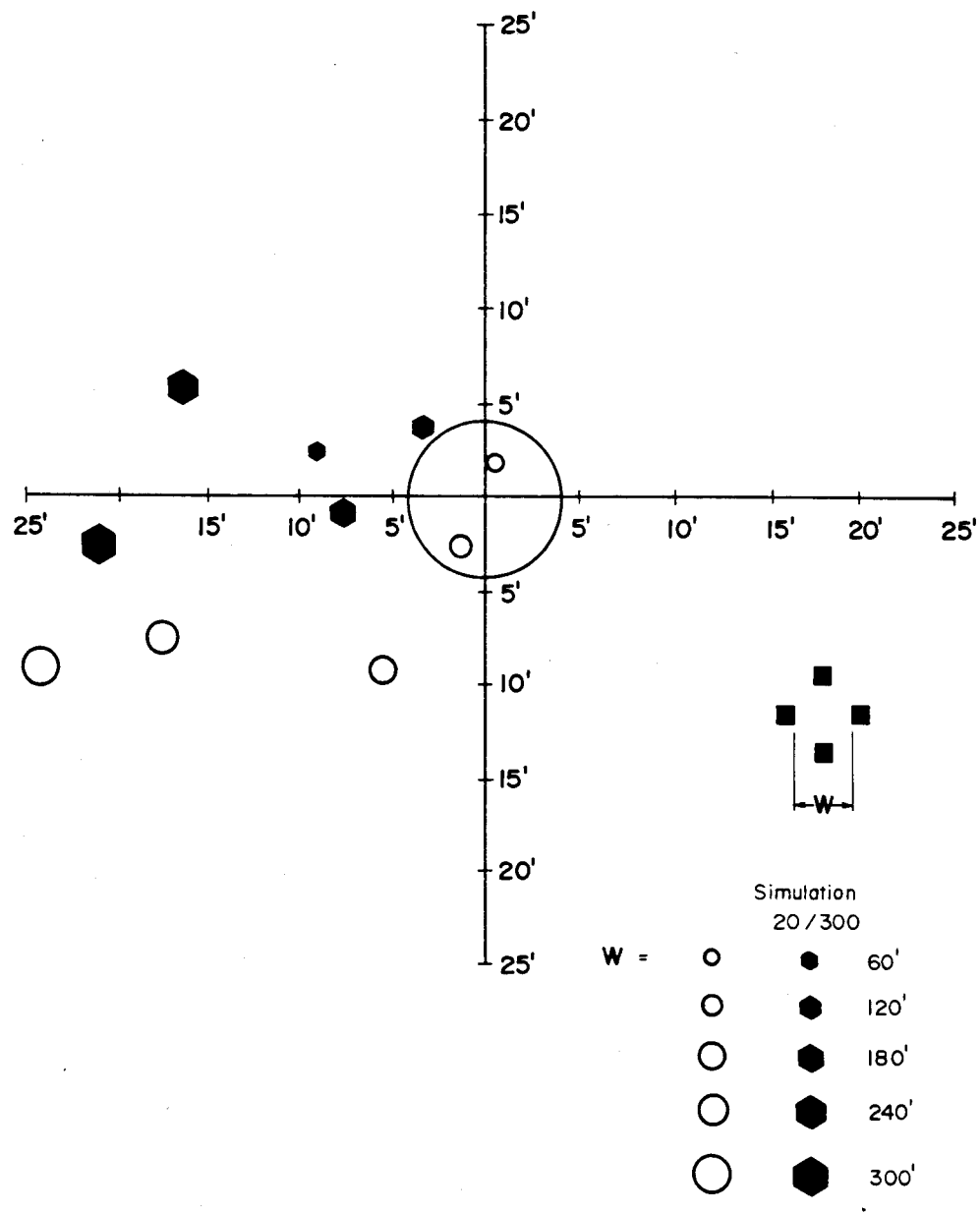
FIG. 3 graphically illustrates results of a test conducted pursuant to a method of this invention.

FIG. 3 graphically illustrates the results of a test carried forth in accordance with the teachings of this invention. The test was conducted on the left eye of a patient exhibiting bilateral myopic retinopathy. While the ocular media were clear, fluid from subretinal hemorrhages in the macular area produced metamorphopsia detectable with the conventional Amsler Grid (OD->OS). Corrected Snellen acuities were OD 20/100, OS 20/40. The results (shown for OS only) include data for "normal viewing" with correction (circles) and under conditions of simulated media opacity (solid hexagons). Different size symbols correspond to different "gap" values used to map the central retina.

Using a substantial degree of simulated opacification which reduced Snellen visual acuity to 20/300, a response level which rendered the conventional Amsler Grid test useless, did not mask the large bias to the left side. The large circle centered on the origin represents the range of values for normal subjects using ground glass to optically degrade their vision to the Snellen equivalent of approximately 20/300.

Figure 4:
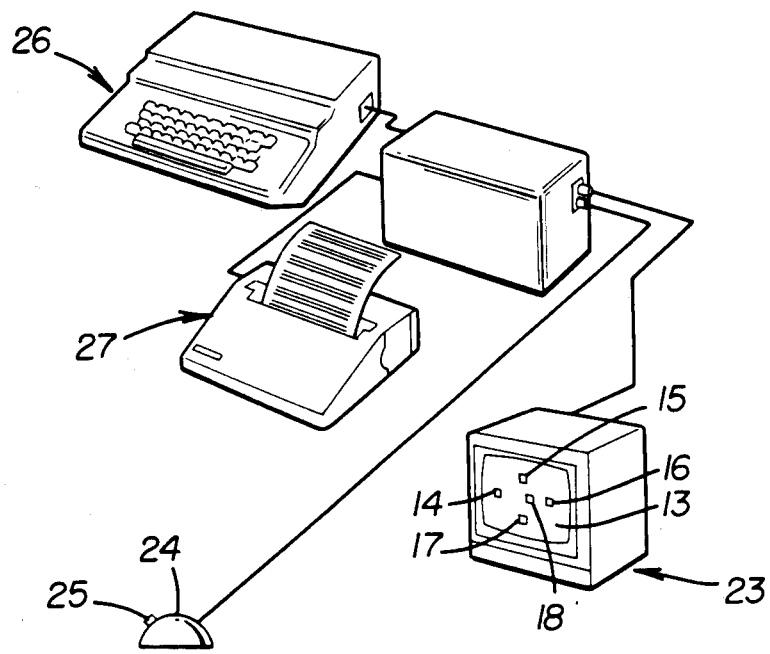
FIG. 4 generally illustrates a microprocessor system for carrying forth a multi-dot hyperacuity bisection task or test.

A microprocessor system and computer program has been developed to allow implementation of a method of this invention on an IBM PC. A nine inch black and white video monitor 23 (FIG. 4) has been used to display spots 14-18 on display screen 13 and a standard Microsoft "mouse" 24 allows the patient to move the central "test" spot 18 (or other element in the pattern) and to depress a "record" button 25, when requested. A joy-stick or other device could be substituted for the "mouse", as will be appreciated by those skilled in the art.

This microprocessor system allows the examiner to have continual access to a computer keyboard 26 and printer 27 during the test session. The stimuli spots, which are preferably bright on a dark background, are preferably square patches of light whose size and luminance can be varied as desired under certain conditions it has proven advantageous to use relatively bright spots on an illuminated background.

Figure 5:
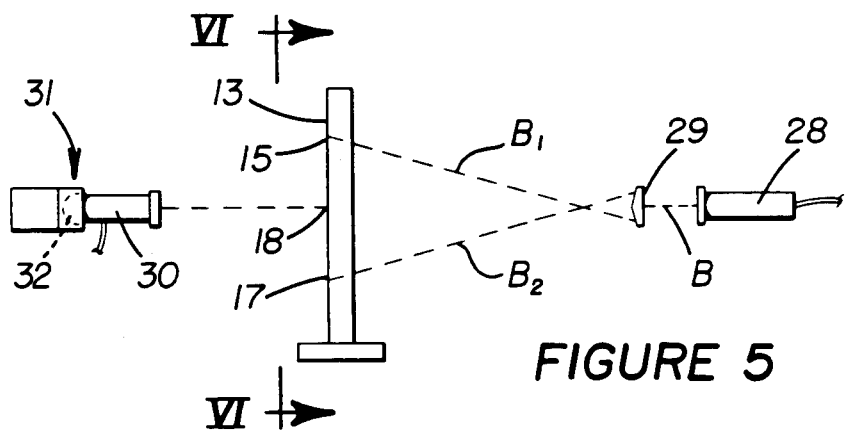
FIG. 5 schematically illustrates apparatus for manually carrying forth such a test.
Figure 6:
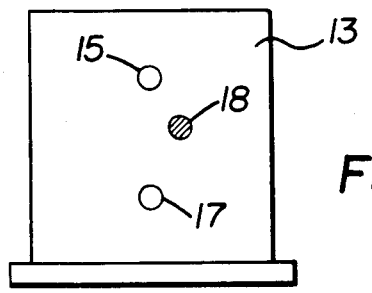
FIG. 6 is a frontal elevational view of a display screen used in the FIG. 5 apparatus, taken in the direction of arrows VI—VI in FIG. 5.

FIGS. 5 and 6 schematically illustrate apparatus for manually carrying forth a method of this invention. In this embodiment, and for illustration purposes, only vertically aligned fixed spots 15 and 17 and moveable spot 18 are displayed on screen 13, i.e., the method of this invention is adapted to use two or more fixed spots for testing purposes. The screen may be composed of a standard translucent ground glass material having the proper imaging qualities to clearly display the laser beam-induced spots.

Fixed spots 15 and 17 are induced by a laser head 28 that emits a single laser beam B of light that is divided into two diverging beams $B_1$ and $B_2$ when it passes through a Maddox bi-prism 29, as described in the above-referenced application. A second prism (not shown) could be suitably positioned on a frontal side of prism 29 to additionally create spots 14 and 16, i.e., to split spots 14 and 16, i.e., to split beams $B_1$ and $B_2$ into four beams.

A second laser head 30 is suitably mounted (on a table or the like, not shown) in a fixed position facing a frontal side of screen 13. Laser head 30 is universally mounted on a stationary mounting member 31, by a ball and socket connection 32, for example. Thus, the patient is enabled to manipulate laser head 30 on instruction from the clinician to selectively move spot 18 on screen 13, relative to fixed spots 15 and 17.

From the above description it is apparent that the new and improved psychophysical hyperacuity testing method of this invention is designed to both detect and quantify retinal distortions (metamorphopsia) even in the presence of substantial media opacities. Examples of this test on a patient, with real metamorphopsia and with a simulated media opacification, show that metamorphopsia can now be detected and quantified even in the presence of severe image degradation caused by pre-retinal opacities.

The scope of testing can be enlarged, such as by placing one or more additional spots at the corners of the pattern or elsewhere. The initial spot tested, the central one, is positioned at the mean location determined for a series of n determinations. To place the corner spots, the patient is asked to fixate (or look at the central spot) and then place a moveable spot in a selected corner (33-36). The spot is then placed at the mean location after n determinations. The test is repeated for the remaining corners.

For example, in FIG. 2, each additional fixed spot 33-36 is shown positioned diagonally relative to the intersection of axes X and Y and in vertical and horizontal alignment relative to other ones of fixed spots 14-17. Thus, when all eight spots 14-17 and 33-36 are utilized an imaginary rectangle intersecting such spots can be defined. In the presence of metamorphopsia, the figure will be distorted from a rectangular form. This additional testing allows quantitative evaluation of the extent of retinal lesions and the detection of decentered lesions.

We claim:

1. A method for evaluating metamorphopsia comprising the steps of
    displaying at least two first spots in fixed and spaced relationship relative to each other on a display screen having imaginary intersecting and perpendicular X and Y axes,
    displaying a second spot on said display screen between said first spots,
    selectively moving said second spot in the direction of one or both of said X and Y axes relative to said first spots for observation and comment by a patient,
    recording said patient's observation and perception of the center position and alignment of said second spot relative to said first spots, and
    measuring and recording the relative separation distances between said second spot and said first spots and the displacement of said second spot relative to an imaginary line intersecting said first spots to determine spatial distortion and evaluation of metamorphopsia.

2. The method of claim 1 wherein said first-mentioned displaying step comprises displaying said two first spots in vertically spaced relationship on said Y axis.

3. The method of claim 1 wherein said first-mentioned displaying step comprises displaying said two first spots in horizontally spaced relationship on said X axis.

4. The method of claim 1 wherein said first-mentioned displaying step comprises displaying a first pair of said first spots in vertically spaced relationship on said Y axis and further displaying a second pair of said first spots in horizontally spaced relationship on said X axis.

5. The method of claim 4 wherein said first-mentioned displaying step comprises displaying at least one third spot diagonally relative to the intersection of said X and Y axes and in alignment relative to at least one of said first spots.

6. The method of claim 5 wherein said first-mentioned displaying step comprises displaying a said third spot at each corner of an imaginary rectangle intersecting said first and third spots.

7. The method of claim 1 wherein said first-mentioned displaying step comprises displaying at least one third spot diagonally relative to the intersection of said X and Y axes.

8. The method of claim 7 wherein said first-mentioned displaying step comprises displaying said third spot in horizontal alignment relative to one of said first spots and in the direction of said X axis.

9. The method of claim 7 wherein said first-mentioned displaying step comprises displaying said third spot in vertical alignment relative to one of said first spots in the direction of said Y axis.

10. Apparatus for evaluating metamorphopsia comprising
    a display screen having imaginary intersecting and perpendicular X and Y coordinates,
    means for displaying at least two first spots in fixed and spaced relationship relative to each other and a second spot between said first spots on said display screen, and
    means for permitting selective movement of said second spot by a patient in the direction of both said X and Y axes relative to said first spots,
    means for recording said patient's observation and perception of the center position and alignment of said second spot relative to said first spots, and
    means for measuring and recording the relative separation distances between said second spot and said first spots and the displacement of said second spot relative to an imaginary line intersecting said first spots to determine spatial distortion and evaluation of metamorphopsia.

* * * * *